(12) United States Patent
Akiyama et al.

(10) Patent No.: US 9,831,077 B2
(45) Date of Patent: Nov. 28, 2017

(54) METHOD FOR ANALYZING EVOLVED GAS AND EVOLVED GAS ANALYZER

(71) Applicant: HITACHI HIGH-TECH SCIENCE CORPORATION, Tokyo (JP)

(72) Inventors: Hideyuki Akiyama, Tokyo (JP); Masafumi Watanabe, Tokyo (JP); Kantaro Maruoka, Tokyo (JP)

(73) Assignee: HITACHI HIGH-TECH SCIENCE CORPORATION, Tokyo (JP)

( * ) Notice: Subject to any disclaimer, the term of this patent is extended or adjusted under 35 U.S.C. 154(b) by 0 days.

(21) Appl. No.: 15/356,580

(22) Filed: Nov. 19, 2016

(65) Prior Publication Data
US 2017/0148616 A1 May 25, 2017

(30) Foreign Application Priority Data

Nov. 20, 2015 (JP) .................................. 2015-227371
Sep. 6, 2016 (JP) .................................. 2016-173396

(51) Int. Cl.
*G01N 27/62* (2006.01)
*G01N 1/38* (2006.01)
(Continued)

(52) U.S. Cl.
CPC ...... *H01J 49/0422* (2013.01); *G01N 30/7206* (2013.01); *H01J 49/10* (2013.01)

(58) Field of Classification Search
CPC ............... G01N 27/264; G01N 27/622; G01N 30/7253; G01N 30/30; G01N 30/32; G01N 30/7213; G01N 30/7273; G01N 30/7286; G01N 30/7293; G01N 1/38; H01J 49/049; H01J 49/022; H01J 49/04; H01J 49/0445; H01J 49/0409; H01J 49/0422; H01J 49/0486; H01J 49/0495; H01J 49/105; H01J 37/08
(Continued)

(56) References Cited

U.S. PATENT DOCUMENTS 4,814,612 A * 3/1989 Vestal ................ G01N 30/7253
250/282
4,883,958 A * 11/1989 Vestal ................ G01N 30/7273
250/281
(Continued)

FOREIGN PATENT DOCUMENTS

JP 2001-28251 A 1/2001
JP 2012-202887 A 10/2012

*Primary Examiner* — David A Vanore
(74) *Attorney, Agent, or Firm* — Maschoff Brennan

(57) ABSTRACT

Disclosed herein is an evolved gas analyzer and a method for analyzing evolved gas, the apparatus enhancing detection accuracy for gas component without providing the apparatus in a large size. The apparatus includes a heating unit evolving a gas component by heating a sample, a detecting means detecting the gas component, a gas channel connecting the heating unit to the detecting means, the gas channel through which mixed gas of the gas component and carrier gas flows, wherein the gas channel includes a branching channel being open to outside and including a discharge flow rate controlling device, and a flow rate control device controlling the discharge flow rate controlling device based on a detection signal received from the detecting means so as to control the detection signal to be within a predetermined range.

21 Claims, 9 Drawing Sheets

(51) Int. Cl.
*H01J 49/04* (2006.01)
*H01J 49/10* (2006.01)
*G01N 30/72* (2006.01)

(58) Field of Classification Search
USPC .... 250/281, 282, 287, 288, 423 R, 424, 425
See application file for complete search history.

(56) References Cited

U.S. PATENT DOCUMENTS

| | | | | |
|---|---|---|---|---|
| 5,367,163 | A * | 11/1994 | Otsuka | H01J 49/105 250/281 |
| 7,928,370 | B2 * | 4/2011 | Amirav | H01J 49/049 250/281 |
| 8,866,075 | B2 * | 10/2014 | Sato | G01N 27/624 250/282 |
| 2006/0192103 | A1 * | 8/2006 | Landgraf | G01N 27/624 250/287 |
| 2008/0128615 | A1 * | 6/2008 | Yamada | H01J 49/0422 250/288 |
| 2012/0326022 | A1 * | 12/2012 | Kumano | H01J 49/0495 250/282 |
| 2013/0277547 | A1 * | 10/2013 | Sato | G01N 27/624 250/282 |

* cited by examiner

METHOD FOR ANALYZING EVOLVED GAS AND EVOLVED GAS ANALYZER

CROSS REFERENCE TO RELATED APPLICATION(S)

This application claims the benefit of Japanese Patent Application No. 2015-227371, filed Nov. 20, 2015, and Japanese Patent Application No. 2016-173396, filed Sep. 6, 2016, which are hereby incorporated by reference in their entirety into this application.

BACKGROUND OF THE INVENTION

1. Technical Field

The present invention relates generally to an evolved gas analyzer and a method for analyzing evolved gas, the method analyzing gas components evolved by heating a sample, thereby identifying, quantifying, etc. the sample.

2. Description of the Related Art

In order to increase flexibility of resins, plasticizers such as phtalates, etc. are added to the resins. After 2019, four substances of the phtalates will be restricted under the restriction of hazardous substances directive (RoHS). Therefore, it is required to identify and quantify the phtalates in the resins.

The phtalates are volatile substances such that a conventional evolved gas analysis (EGA) is applied to analyze the phtalates. The EGA is a method used to analyze gas components evolved by heating a sample by using a gas chromatograph or using various analyzers applying mass spectrometry, etc.

In addition, in the evolved gas analysis, the evolved gas component flows with carrier gas such as nitrogen gas, etc. so as to be introduced into a detecting means. However, when a plurality of gas components are evolved, gas density is too high. Therefore, the gas density exceeds a detection range of a detecting means and thus, a detection signal is overly scaled, whereby the measurement is inaccurate.

Therefore, technology of increasing flow rate of the carrier gas that is mixed with the gas component to dilute the gas component so as to reduce the gas density, when the detection signal of the detecting means exceeds the detection range are disclosed in Patent Documents 1 and 2.

DOCUMENTS OF RELATED ART (Patent Document 1) Japanese Patent Application Publication No. 2001-28251
(Patent Document 2) Japanese Patent Application Publication No. 2012-202887

SUMMARY OF THE INVENTION

However, in case of the Patent Documents 1 and 2, when the gas density is high, it is desired to increase the supply of carrier gas in order to increase flow rate of carrier gas, whereby it results in a large size of the entire apparatus and in an increase of costs.

In addition, when using a mass spectrometer as the detecting means, the gas component is ionized at the front thereof. However, in case of the gas component including an accessory substance, which is not the measurement target, when a plurality of gas components are evolved, a plurality of accessory substances are also ionized. Therefore, substances of the measurement targets are insufficiently ionized, and thus, the detection signal of the measurement target is degraded (ion-suppression). In this case, it is inappropriate to use Patent Documents 1 and 2.

Accordingly, the present invention has been made keeping in mind the above problems occurring in the related art, and an object of the present invention is to provide an evolved gas analyzer and a method for analyzing evolved gas, the apparatus enhancing detection accuracy for the gas component without providing the entire apparatus in a large size.

In order to accomplish the above object, the present invention provides an evolved gas analyzer including: a heating unit evolving a gas component by heating a sample, a detecting means detecting the gas component evolved by the heating unit, and a gas channel making connection between the heating unit and the detecting means in which mixed gas of the gas component and carrier gas, carrying the gas component to the detecting means, flows, wherein the gas channel comprises a gas discharge channel open to outside, the gas discharge channel comprises a discharge flow rate adjusting device, adjusting flow rate of the mixed gas discharged to outside, and the evolved gas analyzer further comprises a flow rate control unit controlling the discharge flow rate adjusting device based on a detection signal from the detecting means so as to bring the detection signal to be within a given range According to the evolved gas analyzer, when a plurality of the gas components are evolved, the gas density is too high. The flow rate of the mixed gas discharged from the branching channel to the outside is increased, and the flow rate of the mixed gas introduced from the gas channel into the detecting means is decreased. Therefore, it is possible to avoid that the gas density exceed the detection range of the detecting means and thus, the detection signal is overly scaled, whereby the measurement is inaccurate.

Here, the flow rate of the mixed gas discharged from the branching channel to the outside is controlled without increasing flow rate of the carrier gas. Therefore, detection accuracy for the gas component may be enhanced without increasing supply of the carrier gas, and without providing the entire apparatus in a large size.

The evolved gas analyzer may include heat retaining unit heating or retaining heat of the gas channel or the branching channel.

According to the evolved gas analyzer, it is possible to prevent the gas component, which is evolved in the heating unit, being cooled, condensed, and trapped at the gas channel or at the inner wall of the branching channel. Therefore, the trapped gas component is not vaporized and is not measured by the detecting means, whereby it is possible to avoid that the measurement is performed for a long time, thus degrading work efficiency. Alternatively, it is possible to prevent the gas component, which is condensed and vaporized, from influencing the next measurement.

The evolved gas analyzer may include a forced discharge unit discharging the mixed gas flowing through the branching channel by force, the forced discharge unit being provided at a discharge side of the branching channel.

According to the evolved gas analyzer, the mixed gas is forced to be discharged, and air pressure of the gas channel and of the branching channel is reduced, whereby the trapped gas component is prevented from flowing backward to the detecting means. Therefore, the trapped gas component is not vaporized and is not measured by the detecting means, whereby it is possible to avoid that the measurement is performed for a long time, thus degrading work efficiency.

Alternatively, it is possible to prevent the gas component, which is condensed and revaporized, from influencing the next measurement.

An angle of a first axis of the gas channel and a second axis of the branching channel may be within a range of 30 to 60 degree angles at a contact point of the gas channel and the branching channel, and the mixed gas may be naturally discharged through the branching channel.

According to the evolved gas analyzer, when the mixed gas is naturally discharged through the branching channel, the mixed gas flowing from upstream of the gas channel does not rapidly change the direction of the mixed gas at the branching channel. Therefore, turbulence is avoided at the branching channel, whereby the mixed gas may be smoothly discharged from the branching channel. In addition, the height of the branching channel is low and thus, space is reduced, in comparison with the case that the angle of the first axis and the second axis is a range of θ>60 degree angles (for example, 90 degree angles).

In addition, when the mixed gas is naturally discharged through the branching channel, the forced discharge unit discharging the mixed gas by force is not provided at the branching channel or at a discharge side of the branching channel. Alternatively, an inlet hole such as a duct, etc. may be provided away from the discharge side of the branching channel. In this case, while operating the duct, flow rate of the mixed gas from the branching channel is set.

The evolved gas analyzer may include a heating control device maintaining the heating unit at a predetermined temperature. The detecting means may be a mass spectrometer.

According to the evolved gas analyzer, the temperature of the heating unit is simply controlled and thus, the measurement is performed for a short time in comparison with a chromatograph, etc. performing detection by changing the temperature of the heating unit.

The evolved gas analyzer may include an ion source provided between the gas channel and a mass spectrometer, the ion source ionizing the gas component of the mixed gas. The detecting means may be the mass spectrometer, and the flow rate control device may control the discharge flow rate controlling device to increase the flow rate of the mixed gas discharged to the outside, when the detection signal received from the detecting means is less than the predetermined range.

When using a mass spectrometer as the detecting means, the gas component is ionized at the ion source, which is placed in front of the detecting means. However, when a plurality of gas components are evolved, a plurality of accessory substances are also ionized. Therefore, substances of the measurement targets are insufficiently ionized, and thus, the detection signal of the measurement target is degraded, which means that ion-suppression occurs, thereby reducing the detection signal.

According to the evolved gas analyzer, in case of the ion-suppression, the flow rate control device determines the peak intensity of the detection signal is less than a threshold value. Next, the flow rate control device controls the discharge flow rate controlling device to increase the flow rate of the mixed gas discharged to the outside. Therefore, the flow rate of the mixed gas introduced into the ion source is reduced, and the ionization of the accessory substances and the degradation of the detection signal are prevented, whereby the detection accuracy for the gas component may be enhanced.

According to another aspect, there is provided a method for analyzing evolved gas, the method including: generating mixed gas by mixing carrier gas and a gas component evolved by heating a sample; introducing the mixed gas into a detecting means through a gas channel; detecting the gas component by using the detecting means; and discharging a portion of the mixed gas from a branching channel open to outside based on a detection signal received from the detecting means so as to control the detection signal to be within a predetermined range, the branching channel being provided with the gas channel.

According to the described above, detection accuracy for the gas component can be enhanced without providing the entire apparatus in a large size.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
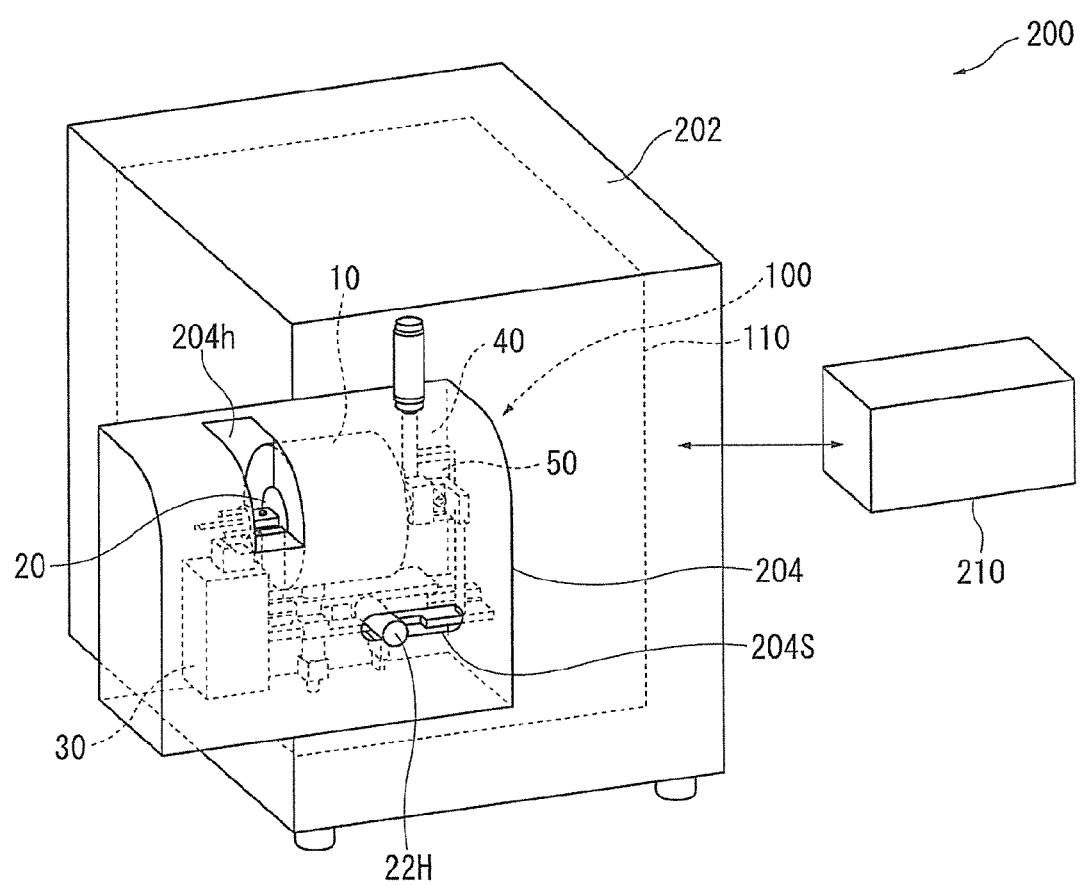
FIG. 1 is a perspective view showing the configuration of an evolved gas analyzer according to an exemplary embodiment of the present invention.
Figure 2:
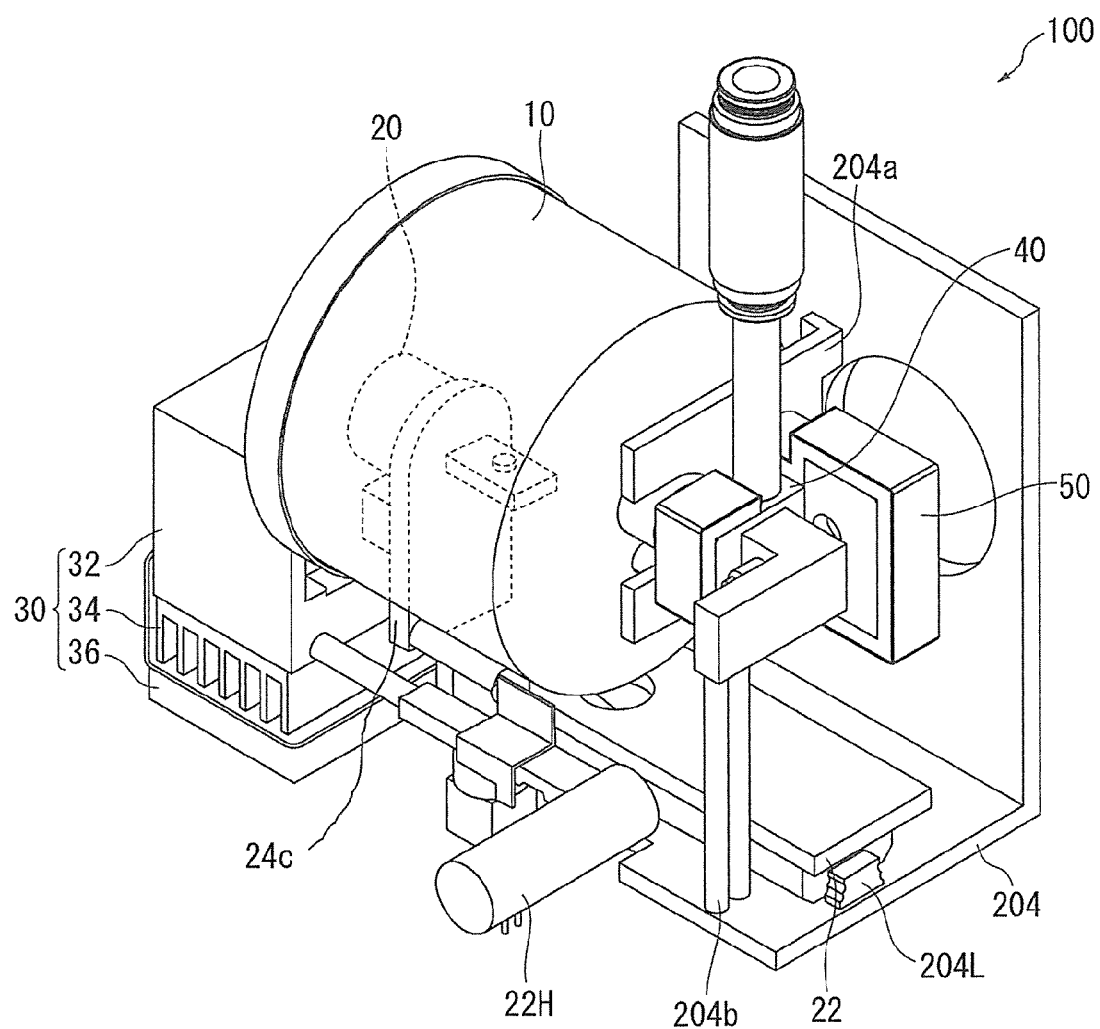
FIG. 2 is a perspective view showing the configuration of a gas evolving unit.
Figure 3:
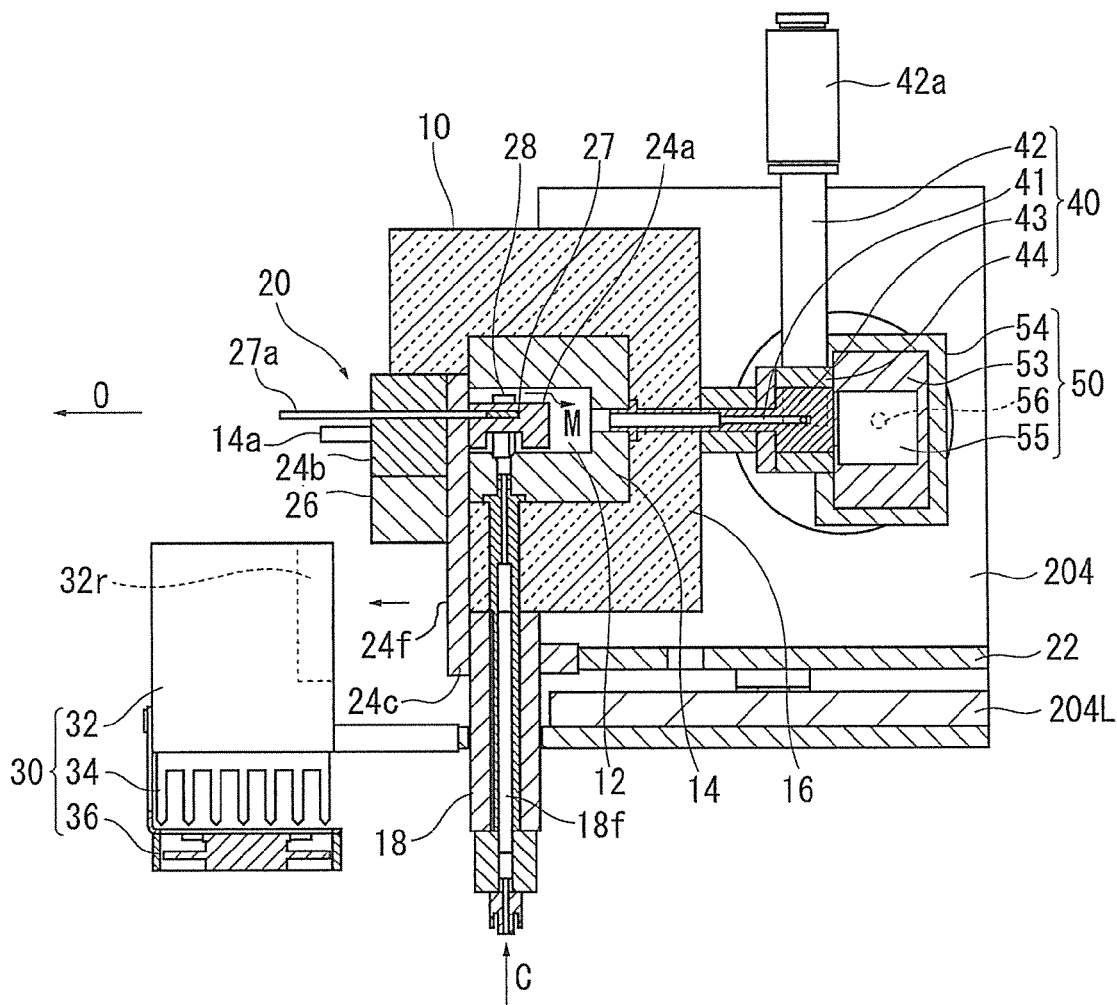
FIG. 3 is a longitudinal sectional view showing the configuration of the gas evolving unit.
Figure 4:
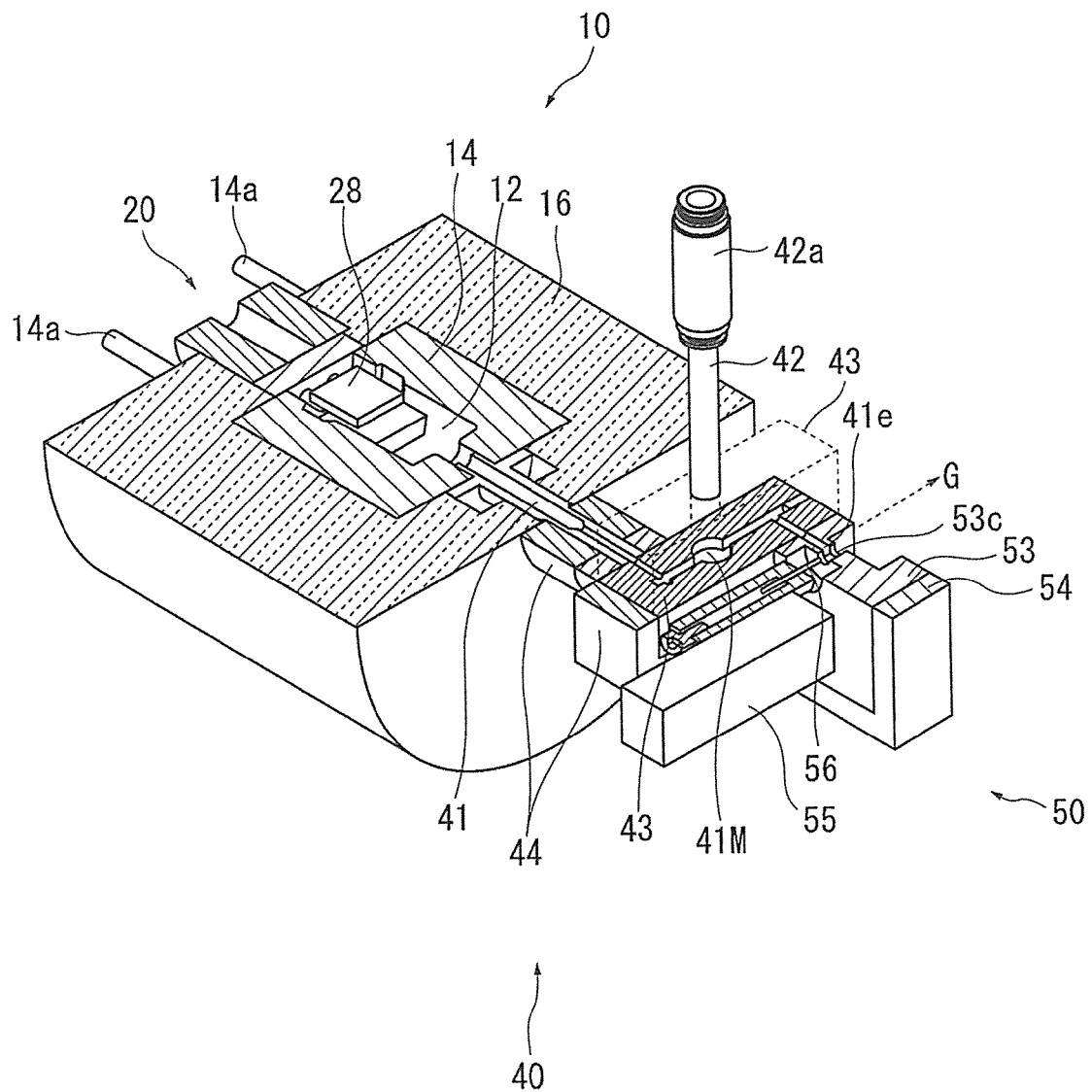
FIG. 4 is a cross-sectional view showing the configuration of the gas evolving unit.

Hereinafter, the exemplary embodiment of the present invention will be described with reference to the accompanying drawings. FIG. 1 is a perspective view showing the configuration of an evolved gas analyzer 200. FIG. 2 is a perspective view showing the configuration of a gas evolving unit 100. FIG. 3 is a longitudinal sectional view showing the configuration of the gas evolving unit 100 on an axis O. FIG. 4 is a cross-sectional view showing the configuration of the gas evolving unit 100 on the axis O.

The evolved gas analyzer 200 includes a body unit 202 that is a housing; an attaching unit 204 for a gas evolving unit, the attaching unit having a box shape and attached at a front surface of the body unit 202; and a computer (control device) 210 controlling the evolved gas analyzer. The computer 210 includes a CPU processing data, a memory unit storing a computer program and data, an input unit such as a monitor, a keyboard, etc.

In the attaching unit 204 for the gas evolving unit, there are a heating furnace (heating unit) 10 having a cylinder shape; a sample holder 20; a cooling unit 30; a splitter 40 splitting gas; and the gas evolving unit 100 having an ion source 50 as assembly. In addition, a mass spectrometer (detecting means) 110 is provided in the body unit 202. The mass spectrometer analyses gas components evolved by heating a sample.

In addition, an opening 204h is provided at an upper surface of the attaching unit 204 for the gas evolving unit, while being provided at a front surface thereof. The sample holder 20 is located at the opening 204h by being moved toward a discharging position that is located at an outside of the heating furnace 10. Therefore, a sample may be supplied on or removed from the sample holder 20 through the opening 204h. In addition, a slit 204s is provided at the front surface of the attaching unit 204. By moving an opening/closing handle 22H exposed to an outside of the attaching unit through the slit, the sample holder 20 is moved into or from the heating furnace 10. Therefore, the sample holder is set at the discharging position, and thus, the sample is supplied on or removed from the sample holder.

In addition, for example, when the sample holder 20 is moved on a movement rail 204L by a stepping motor, etc. controlled by the computer 210, the sample holder 20 may be automatically moved into or from the heating furnace 10.

Hereinafter, the configuration of the gas evolving unit 100 will be described with reference to FIGS. 2 to 5.

First, the heating furnace 10 is attached to an attaching plate 204a of the attaching unit 204 by being parallel to the axis O. The heating furnace includes a heating chamber 12 having a cylinder shape and being opened on the axis O; a heating block 14; and a heat retaining jacket 16.

The heating block 14 surrounds the heating chamber 12, and the heat retaining jacket 16 surrounds the heating block 14. The heating block 14 is made of aluminum, and is heated by electricity from a pair of heating unit heaters 14a extending from the heating furnace 10 to outside in a direction of the axis O as shown in FIG. 4.

In addition, the attaching plate 204a extends in a direction perpendicular to the axis O. The splitter 40 and the ion source 50 are attached to the heating furnace 10. In addition, a supporter 204b extends in a vertical direction of the attaching unit 204, and supports a staying unit 55 of the ion source 50.

The splitter 40 is connected to an opposite side (right side of FIG. 3) of an opening side of the heating furnace 10. In addition, a carrier gas protecting pipe 18 is connected to a lower side of the heating furnace 10. The carrier gas protecting pipe 18 surrounds a carrier gas channel 18f connected to a lower surface of the heating chamber 12. Carrier gas C is introduced into the heating chamber 12 through the carrier gas channel.

In addition, a gas channel 41 communicates with a cross section on the opposite side (right side of FIG. 3) of an opening side of the heating chamber 12. Mixed gas M of the carrier gas C and a gas component G evolved by the heating furnace 10 (heating chamber 12) flows through the gas channel 41.

The sample holder 20 includes a stage 22 moving on the movement rail 204L attached to an inner upper surface of the attaching unit 204; a bracket 24c attached on the stage 22 and extending in a vertical direction; insulators 24b and 26 attached to a front surface (left side of FIG. 3) of the bracket 24c; a sample holding unit 24a extending from the bracket 24c in a direction of the axis O in the heating chamber 12; a sample heater 27 provided just below the sample holding unit 24a; and a sample plate 28 provided on an upper surface of the sample holding unit 24a above the sample heater 27, the sample plate on which the sample is placed.

Here, the movement rail 204L extends in a direction of the axis O (horizontal direction of FIG. 3), and the stage 22 of the sample holder 20 moves in the direction of the axis O. In addition, the opening/closing handle 22H extends in a direction perpendicular to the axis O, and is attached to the stage 22.

In addition, an upper portion of the bracket 24c has a semicircular shape and a lower portion of the bracket has a rectangular shape. Referring to FIG. 2, the insulator 24b has a substantially cylinder shape, and is provided at a front surface of an upper portion of the bracket 24c. An electrode 27a of the sample heater 27 penetrates the insulator 24b, and protrudes to an outside of the gas evolving unit. The insulator 26 has a rectangular shape, and is provided at the front surface of the bracket 24c. The insulator 26 is located lower than the insulator 24b. In addition, the insulator 26 is not provided at a lower portion of the bracket 24c, and a front surface of the lower portion of the bracket 24c is exposed to form a contact surface 24f.

The bracket 24c has a diameter slightly larger than a diameter of the heating chamber 12 such that the bracket 24c seals the heating chamber 12. The sample holding unit 24a is located in the heating chamber 12.

In addition, the sample placed on the sample plate 28 in the heating chamber 12 is heated in the heating furnace 10 such that the gas component G is evolved.

The cooling unit 30 faces the bracket 24c of the sample holder 20, and is located at an outside of the heating furnace 10 (left side of the heating furnace 10 in FIG. 3). The cooling unit 30 includes a cooling block 32 having a concave portion 32r that has a rectangular shape; cooling fins 34 connected to a lower surface of the cooling block 32; and a pneumatic cooling fan 36 connected to a lower surface of the cooling fins 34, and blowing air to the cooling fins 34.

In addition, when the sample holder 20 moves in a direction of the axis O on the movement rail 204L toward a left side of FIG. 3, and comes out of the heating furnace 10, the contact surface 24f of the bracket 24c is positioned at the concave portion 32r of the cooling block 32 by being in contact with the concave portion. Consequently, as heat of the bracket 24c is removed by the cooling block 32, the sample holder 20 (particularly, the sample holding unit 24a) is cooled.

In addition, according to the exemplary embodiment of the present invention, the sample holder 20 (including the bracket 24c) and the cooling block 32 are made of aluminum.

As shown in FIGS. 3 and 4, the splitter 40 includes the gas channel 41 connected to the heating chamber 12; a branching channel 42 connected to the gas channel 41, and opened to the outside; a mass flow controller (discharged flow rate controlling device) 42a connected to a discharge side of the branching channel 42 to control flow rate of the mixed gas M discharged from the branching channel 42 to the outside; a housing unit 43 opening the gas channel 41 therein; and a heat retaining unit 44 surrounding the housing unit 43.

As shown in FIG. 4, when viewed from the top, the gas channel 41 is connected to the heating chamber 12 and extends in a direction of the axis O and next, bends in a direction perpendicular to the axis O, and bends again in a direction of the axis O such that the gas channel reaches an end part 41e. The gas channel has a crank shape. In addition, a portion of the gas channel 41 that extends in a direction perpendicular to the axis O is provided with a center thereof having a circular shape that has a diameter larger that a diameter of the gas channel to define a branch chamber 41M. The branch chamber 41M extends to an upper surface of the housing unit 43. The branch chamber 41M is fitted with the branching channel 42 having a diameter slightly smaller than that of the branch chamber 41M.

The gas channel 41 may have a straight line shape extending in a direction of axis O from the heating chamber 12 connected with the gas channel to the end part 41e. Alternatively, depending on a positional relationship with the heating chamber 12 or with the ion source 50, the gas channel 41 may have a various curved shape, a line shape having an angle to the axis O, etc.

In addition, according to the exemplary embodiment of the present invention, the gas channel 41 has a diameter about 2 mm, and the branch chamber 41M and the branching channel 42 have respective diameters about 1.5 mm. In addition, a ratio (split ratio) of flow rates from the gas channel 41 to the end part 41e, and flow rates branched to the branching channel 42 is determined by a flow resistance. The mixed gas M may flow more through the branching channel 42. In addition, the split ratio is controlled by adjusting an opening ratio of the mass flow controller 42a.

In addition, the inner diameter of the branching channel 42 is determined to provide that the sum of cross sectional areas of the gas channel being in contact with the ion source and the branching channel is less than a cross sectional area of the gas channel positioned just before the branching channel. In addition, the inner diameter of the branching channel 42 is determined to avoid the flow rate of the mixed gas from being reaching the speed of sound at any position of the gas channel being in contact with the ion source and the branching channel. It is desired that the inner diameter of the branching channel is 50~90% of the inner diameter of the gas channel 41 positioned just before the contact potion P (referring to FIG. 9).

As shown in FIGS. 3 and 4, the ion source 50 includes an ionizer housing unit 53; an ionizer heat retaining unit 54 surrounding the ionizer housing unit 53; a discharge needle 56; and a staying unit 55 fixing the discharge needle 56. The ionizer housing unit 53 has a plate shape, and a surface of the plate is parallel to the axis O. A small hole 53C penetrates the center of the surface of the plate. In addition, the end part 41e of the gas channel 41 passes through the ionizer housing unit 53, and faces a side wall of the small hole 53C. In the meantime, the discharge needle 56 extends in a direction perpendicular to the axis O, and faces the small hole 53C.

In addition, in the mixed gas M introduced around the small hole 53C from the end part 41e, the gas component G is ionized by the discharge needle 56.

The ion source 50 is a well-known device. According to the exemplary embodiment of the present invention, atmospheric pressure chemical ionization (APCI) is applied to the ion source. APCI causes minimal fragmentation of the gas component G, such that fragmentation peak does not occur. Therefore, it is possible to detect the measurement target without separating the gas component G by using a chromatograph, etc.

The gas component G ionized at the ion source 50 and the carrier gas C are introduced to the mass spectrometer 110, and are analyzed.

In addition, the ion source 50 is contained in the ionizer heat retaining unit 54.

Figure 5:
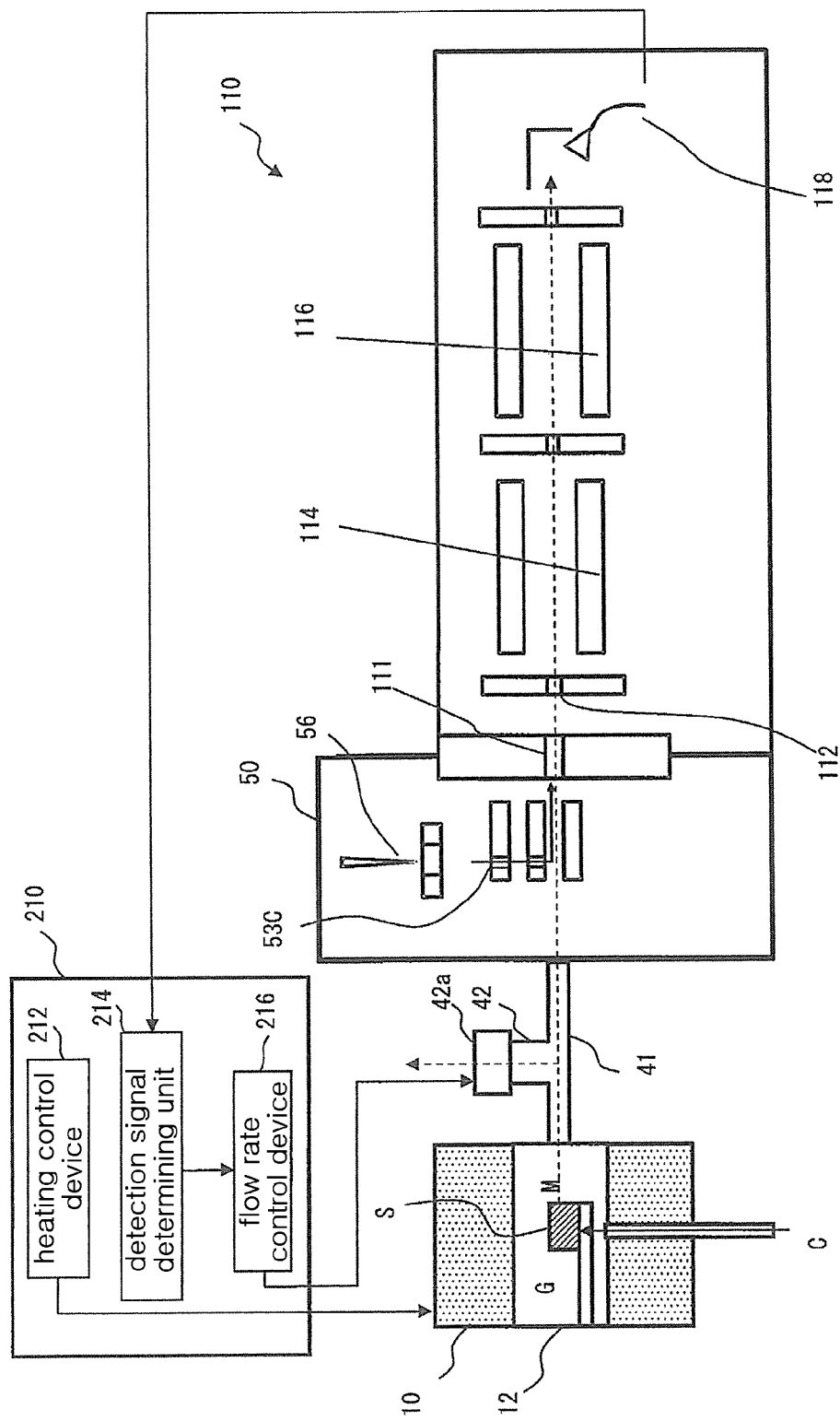
FIG. 5 is a block diagram showing a process of analyzing a gas component by the evolved gas analyzer.

FIG. 5 is a block diagram showing a process of analyzing a gas component by the evolved gas analyzer 200.

The sample S is heated in the heating chamber 12 of the heating furnace 10, and the gas component G is evolved. Heating condition (temperature rising rate, maximum temperature, etc.) of the heating furnace 10 is controlled by a heating control device 212 of the computer 210.

The gas component G is mixed with the carrier gas C introduced in the heating chamber 12 to be a mixed gas M, and the mixed gas M is introduced in the splitter 40. A detection signal determining unit 214 of the computer 210 receives a detection signal from a detector 118 of the mass spectrometer 110.

A flow rate control device 216 determines whether or not peak intensity of the detection signal received from the detection signal determining unit 214 is within a threshold range. When the peak intensity is out of the threshold range, the flow rate control device 216 controls the opening ratio of the mass flow controller 42a. Therefore, flow rate of the mixed gas M discharged from the splitter 40 to an outside through the branching channel 42 is controlled, and further, flow rate of the mixed gas M introduced from the gas channel 41 into the ion source 50 is controlled, thereby optimizing a detection accuracy of the mass spectrometer 110.

The mass spectrometer 110 includes a first fine hole 111 through which the gas component G ionized at the ion source 50 is introduced; a second fine hole 112 through which the gas component G flows, after the first fine hole 111; an ion guide 114; a quadrupole mass filter 116; and the detector 118 detecting the gas component G discharged from the quadrupole mass filter 116.

The quadrupole mass filter 116 varies an applied high frequency voltage such that mass is scanned. The quadrupole mass filter generates a quadrupole electric field, and detects ions by moving the ions like a pendulum swinging within the quadrupole electric field. The quadrupole mass filter 116 functions as a mass separator passing only gas component G within a certain mass range such that the detector 118 may identify and quantify the gas component G.

In addition, in comparison with an entire ions detection (scan) mode detecting ions of a certain range of a mass-to-charge ratio, when using a selected ion detection (SIM) mode detecting only ions of a certain mass-to-charge ratio m/z of a gas component, which is a measurement target, a detection accuracy of the gas component, which is the measurement target, increases.

Figure 6A:
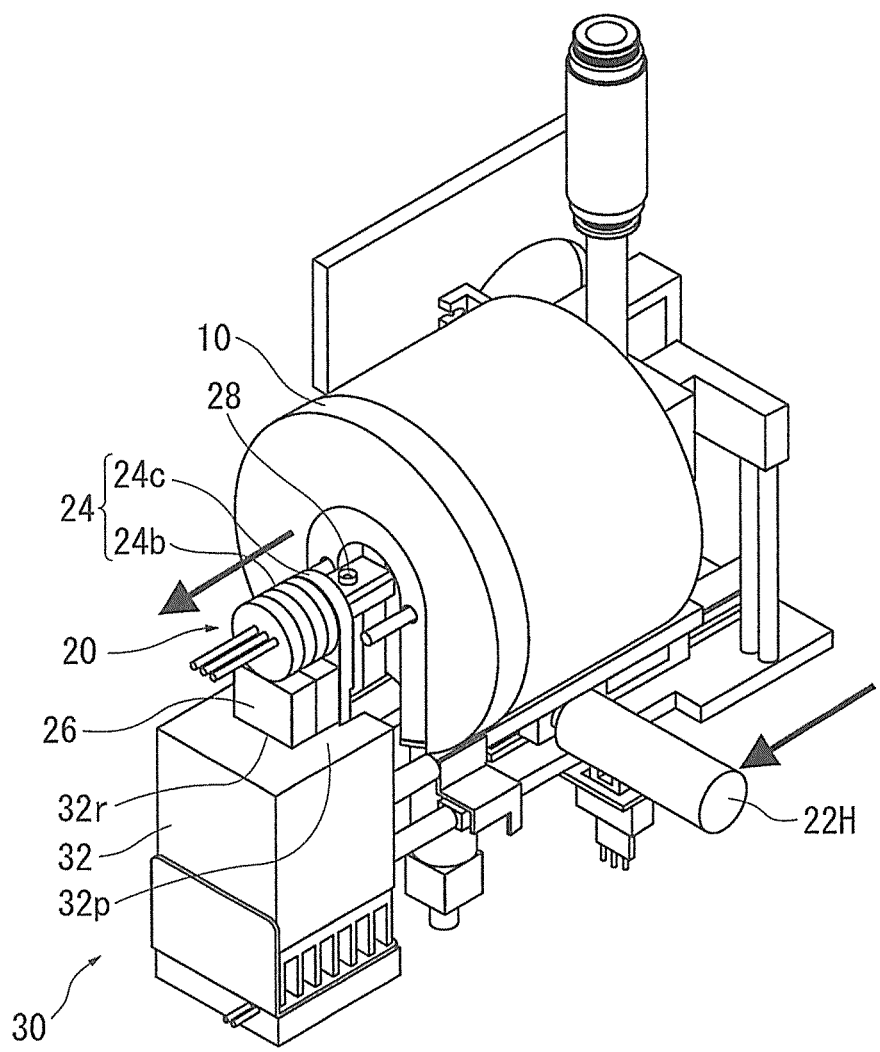
FIGS. 6A and 6B are views respectively showing a discharging position and a measuring position of the sample holder.
Figure 6B:
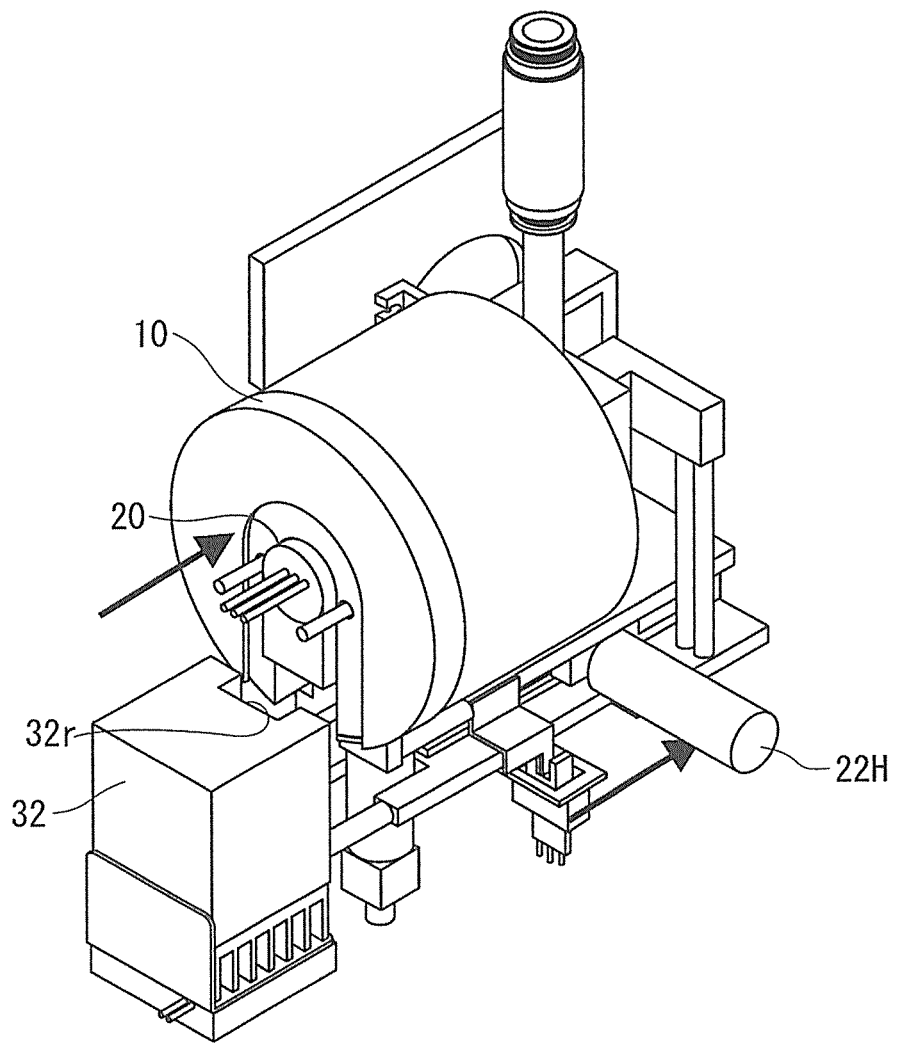

In addition, as shown in FIGS. 6A and 6B, according to the exemplary embodiment of the present invention, the stage 22 moves the sample holder 20 in the direction of axis O between predetermined two positions (a discharging position which is located at the outside of the heating furnace 10 where the sample plate 28 is discharged as shown in FIG. 6A, and a measuring position at which the gas component is measured is located in the heating furnace 10 where the sample plate 28 is received therein as shown in FIG. 6B).

Therefore, the sample and the sample plate 28 are supplied on or removed from the sample holder at the discharging position of FIG. 6A. Here, the contact surface 24f of the bracket 24c is in contact with the concave portion (contact portion) 32r of the cooling block 32. Therefore, heat of the bracket 24c is cooled by the cooling block 32, and thus the sample holder 20 is cooled.

According to the exemplary embodiment of the present invention, as shown in FIGS. 3 and 4, the gas channel 41 includes a branching channel 42 opened to the outside. An opening ratio of a mass flow controller 42a attached to the branching channel 42 is controlled to adjust flow rate of the mixed gas M discharged from the branching channel 42 to the outside, and to adjust flow rate of the mixed gas M introduced from the gas channel 41 into the ion source 50.

Therefore, when a plurality of gas components are evolved and thus, gas density is too high, the flow rate of the mixed gas M discharged from the branching channel 42 to the outside is increased, and the flow rate of the mixed gas M introduced from the gas channel 41 into the ion source 50 is decreased. Therefore, it is possible to avoid that the gas density exceeds the detection range of the mass spectrometer 110, whereby the detection signal is overly scaled and the measurement is inaccurate.

Here, the flow rate of the mixed gas discharged from the branching channel 42 to the outside is controlled without increasing flow rate of the carrier gas. Therefore, detection accuracy for the gas component may be enhanced without increasing supply of the carrier gas, and without providing the entire apparatus in a large size.

In addition, when using the mass spectrometer as the detecting means, the gas component is ionized at the front thereof, which is the ion source 50. However, when the plurality of gas components are evolved, accessory substances are ionized. Thus, ion-suppression occurs, and the detection signal is degraded.

Therefore, in case of the ion-suppression, the flow rate control device 216 determines the peak intensity of the detection signal of the mass spectrometer 110 received from the detection signal determining unit 214 is less than a threshold value. Next, the flow rate control device 216 transmits a control signal to the mass flow controller 42a to increase the opening ratio. Therefore, the flow rate of the mixed gas M introduced into the ion source 50 is reduced, and the ionization of the accessory substances and the degradation of the detection signal are prevented, whereby the detection accuracy for the gas component may be enhanced.

In addition, it is difficult to determine whether or not the ion-suppression occurs by only obtaining the peak intensity of the detection signal. Also, the measurement target may have a low content of the gas component. Therefore, it is required to determine whether or not ion-suppression occurs due to high content of a concomitant, etc. that is not the measurement target. The determination is performed by a user or the flow rate control device 216 based on a table storing that whether or not ion-suppression occurs at each sample or at each gas component.

In addition, the flow rate control device 216 generates a control signal to increase the flow rate of the mixed gas M discharged from the branching channel 42 to the outside, when the peak intensity of the detection signal exceeds the threshold value (overly scaled) or is less than the threshold value (when determining that ion-suppression occurs).

In this case, for example, the table stores that whether or not ion-suppression occurs at each gas component, and the flow rate control device 216 determines the ion-suppression based on the table. When determining that ion-suppression occurs, a control signal for increasing the opening ratio is transmitted to the mass flow controller 42a. In addition, whenever the measurement is conducted the user input whether the measurement causes ion-suppression or not, using an input unit (select button, etc.) of the computer 210. The flow rate control device 216 compares the peak intensity of the detection signal with the threshold value based on the input signal, and transmits a control signal for increasing the opening ratio to the mass flow controller 42a.

In addition, when the measurement target is phtalates and the accessory substance is additive agent of phthalate, etc., ion-suppression occurs.

In addition, the gas component evolved in the heating furnace 10 may be cooled, condensed, and trapped at the gas channel 41 located close to the branch chamber 41M and at an inner wall of the branching channel 42, and next, may be vaporized and measured in the ion source 50. In this case, a long period is required for measurement, thus work efficiency is degraded. In addition, the gas component, which is condensed and vaporized, may influence the next measurement.

Figure 7:
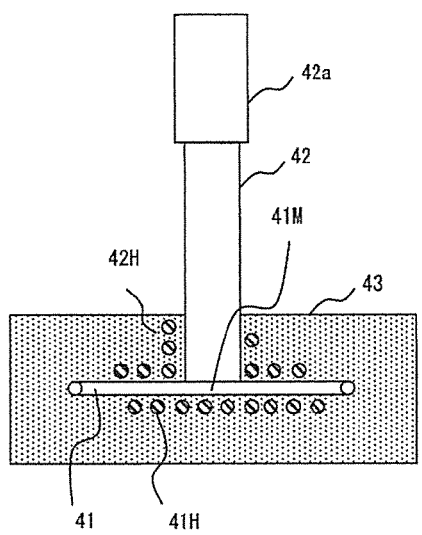
FIG. 7 is a view showing a gas channel and heat retaining unit of a branching channel.

Therefore, as shown in FIG. 7, heat retaining unit 41H and 42H may be provided to heat or retain the heat of the perimeter of at least one of the gas channel 41 located close to the branch chamber 41M and the branching channel 42. Therefore, it is possible to prevent the gas component being trapped at the gas channel 41 or at the inner wall of the branching channel 42.

In addition, referring to FIG. 7, the heat retaining part 41H is a coil heater heating the perimeter of the gas channel 41 located close to the branch chamber 41M, and the heat retaining part 42H is a coil heater heating the perimeter of the branching channel 42 located close to the branch chamber 41M.

In addition, the heat retaining unit 41H and 42H are not limited to heaters, and may be an insulator, etc. that can prevent coagulation of the gas component. In addition, it is possible to provide at least one of the heat retaining unit 41H and 42H, or both.

In the meantime, when the gas component (mixed gas) is heated by the heat retaining unit 41H and 42H, the mixed gas discharged from the branching channel 42 and flowing through the mass flow controller 42a starts to have high temperature. Therefore, a heating resisting type mass flow controller 42a may be required.

Figure 8:
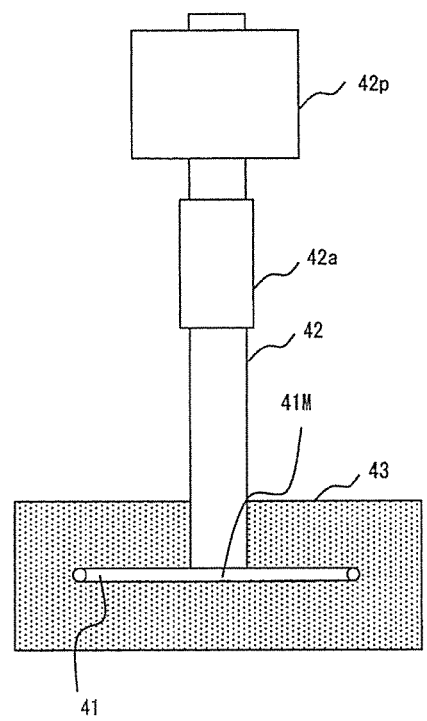
FIG. 8 is a view showing a forced discharge unit of the branching channel.

Therefore, as shown in FIG. 8, instead of providing the heat retaining unit 41H and 42H, a discharge pump (forced discharge unit) 42p may be provided at the branching channel 42, which is closer to the outgoing side than the mass flow controller (42a). By this, the air pressure in the gas channel 41 located close to the branch chamber 41M and the branching channel 42 is lowered from discharging the mixed gas M flowing through the branching channel 42 by force through this, so the trapped gas component is prevented from flowing back to the ion source 50.

Figure 9:
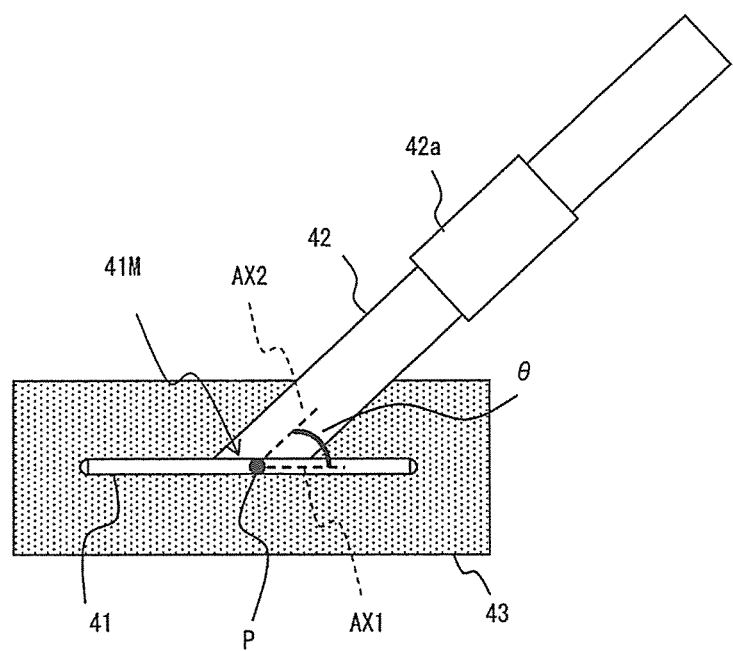
FIG. 9 is a view showing a gas channel and heat retaining unit according to another exemplary embodiment of the present invention.

In addition, as shown in FIG. 9, at a contact point P (contact portion) of the gas channel 41 and the branching channel 42 that are located around the branch chamber 41M, an angle θ of a first axis AX1 (an axis of the gas channel 41) and a second axis AX2 (an axis of the branching channel 42) is within a range of 30 to 60 degree angles. The mixed gas is naturally discharged through the branching channel 42.

According to the described above, when the mixed gas is naturally discharged through the branching channel 42, the mixed gas M flowing from upstream of the gas channel 41 does not rapidly change the direction of the mixed gas at the branching channel 42. Therefore, turbulence is avoided at the branching channel 42, whereby the mixed gas may be smoothly discharged from the branching channel 42. In addition, the height of the branching channel 42 is low and thus, the space is reduced, in comparison with the case that the angle of the first axis and the second axis is a range of θ>60 degree angles (for example, 90 degree angles). In addition, when the angle of the first axis and the second axis is a range of θ<30 degree angles, the turbulence may be avoided. However, the branching channel 42 is almost horizontal, such that sufficient space is required therefor. In addition, when the branching channel 42 is long, the gas component may be trapped in the branching channel 42. Moreover, it is difficult to heat the branching channel 42. Therefore, the angle θ of the first axis and the second axis is equal to or greater than 30 degree angles.

Here, the branching channel 42 of FIG. 9 is provided to enter the housing unit of FIG. 3.

In addition, flow rate of the mixed gas at an introduction side the branching channel 42 having the angle θ of the first axis and the second axis at the range of 30 to 60 degree angles may be, for example, 0.5~2 ml/min, without being limited thereto.

In addition, the contact potion P is an intersection point of the center-lines of the gas channel 41 and of the branching channel 42. In addition, at the contact potion P, when the angle θ of the first axis AX1 and the second axis AX2 is a range of 30 to 60 degree angles, an angle of an axis of the gas channel 41 and an axis of the branching channel 42 that are located downstream of the contact potion P may be beyond the range of 30 to 60 degree angles.

In addition, "the branching channel discharges naturally" means not providing a device changing the flow rate in the branching channel 42 (a discharge pump 42*p* of FIG. 8, etc.) at the branching channel 42, which is closer to the outgoing side than the mass flow controller (42*a*).

In addition, the contact potion P is located at a position of the gas channel 41 in which flow of gas is uniform.

It should be understood that the exemplary embodiment according to the concept of the present invention is not limited to the exemplary embodiment, but various modifications, equivalents, additions and substitutions are possible, without departing from the scope and spirit of the invention.

Besides phtalates, the measurement target may be brominated flame retardants (polybrominated biphenyl (PBB), polybrominated diphenyl ether (PBDE)) restricted under RoHS, without being limited thereto.

Components, shapes, configurations, etc. of the gas channel 41, the branching channel 42, and the splitter 40 are not limited to the exemplary embodiments. In addition, the detecting means is not limited to the mass spectrometer.

What is claimed is:

1. An evolved gas analyzer comprising:
    a heating unit evolving a gas component by heating a sample,
    a detecting means detecting the gas component evolved by the heating unit, and
    a gas channel making connection between the heating unit and the detecting means in which mixed gas of the gas component and carrier gas, carrying the gas component to the detecting means, flows,
    wherein the gas channel comprises a branching channel open to outside, the branching channel comprises a discharge flow rate controlling device, adjusting flow rate of the mixed gas discharged to outside, and the evolved gas analyzer further comprises a flow rate control device controlling the discharge flow rate controlling device based on a detection signal from the detecting means so as to bring the detection signal to be within a given range.

2. The apparatus of claim 1, further comprising a heat retaining unit, heating or retaining heat of the gas channel or the branching channel.

3. The apparatus of claim 1, further comprising:
    a forced discharge unit, discharging the mixed gas flowing in the branching channel by force, on a discharge side of the branching channel.

4. The apparatus of claim 1, wherein an angle between a first axis of the gas channel at a point of contact with the branching channel and a second axis of the branching channel at a point of contact with the gas channel is between 30 to 60 degrees and the branching channel discharges naturally.

5. The apparatus of claim 2, wherein an angle between a first axis of the gas channel at a point of contact with the branching channel and a second axis of the branching channel at a point of contact with the gas channel is between 30 to 60 degrees and the branching channel discharges naturally.

6. The apparatus of claim 1, further comprising a heating control device maintaining the heating unit at a certain temperature, wherein the detecting means is a mass spectrometer.

7. The apparatus of claim 2, further comprising a heating control device maintaining the heating unit at a certain temperature, wherein the detecting means is a mass spectrometer.

8. The apparatus of claim 3, further comprising a heating control device maintaining the heating unit at a certain temperature, wherein the detecting means is a mass spectrometer.

9. The apparatus of claim 4, further comprising a heating control device maintaining the heating unit at a certain temperature, wherein the detecting means is a mass spectrometer.

10. The apparatus of claim 5, further comprising a heating control device maintaining the heating unit at a certain temperature, wherein the detecting means is a mass spectrometer.

11. The apparatus of claim 1, wherein the detecting means is a mass spectrometer, the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

12. The apparatus of claim 2, wherein the detecting means is a mass spectrometer, the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

13. The apparatus of claim 3, wherein the detecting means is a mass spectrometer, the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

14. The apparatus of claim 4, wherein the detecting means is a mass spectrometer, the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

15. The apparatus of claim 5, wherein the detecting means is a mass spectrometer, the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

16. The apparatus of claim 6, wherein the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

17. The apparatus of claim 7, wherein the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

18. The apparatus of claim 8, wherein the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

19. The apparatus of claim 9, wherein the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

20. The apparatus of claim 10, wherein the evolved gas analyzer further comprises an ion source between the gas channel and the mass spectrometer, ionizing the gas component of the mixed gas, and the flow rate control device controls the discharge flow rate controlling device to increase the discharge flow rate of the mixed gas when a detection signal from the detecting means is outside the given range.

21. A method for analyzing evolved gas, comprising:
generating mixed gas by mixing a gas component evolved by heating a sample with carrier gas,
introducing the mixed gas into a detecting means through a gas channel,
detecting the gas component with the detecting means, and
discharging a portion of the mixed gas to outside from a branching channel installed on the gas channel and open to outside based on a detection signal from the detecting means so as to bring the detection signal to be within a given range.

* * * * *